United States Patent

Mura

[11] Patent Number: 5,835,191
[45] Date of Patent: Nov. 10, 1998

[54] OPTOTYPE PROJECTOR APPARATUS WITH VARIABLE CONTRAST

[76] Inventor: Sergio Mura, 14, via Mameli, Scandicci, Italy

[21] Appl. No.: 735,016

[22] Filed: Oct. 22, 1996

[51] Int. Cl.$^6$ ........................................................ A61B 3/02
[52] U.S. Cl. ............................................ 351/237; 351/243
[58] Field of Search ................................... 351/222, 236, 351/237, 239, 243, 245, 211

[56] References Cited

U.S. PATENT DOCUMENTS

| | | | |
|---|---|---|---|
| 3,684,355 | 8/1972 | Molner | 351/243 |
| 4,155,632 | 5/1979 | Wolbarsht | 351/243 |
| 4,572,630 | 2/1986 | Task et al. | 351/243 |
| 4,861,156 | 8/1989 | Terry | 351/243 |

*Primary Examiner*—Huy Mai
*Attorney, Agent, or Firm*—McAulay Fisher Nissen Goldberg & Kiel, LLP

[57] ABSTRACT

An optotype projector apparatus provided with variable contrast, and having a large variety of optotypes and matrices for providing tests for stereoscopic vision of chromatic balance and comprising a projector for producing contrasting variations of the optotype images operating on the basis of two complementary light sources, one provided by a primary body and the other provided by a secondary body, both of which are remotely controlled so that by diminishing the intensity of one source, a consequent increase of the other source takes place. The primary body is provided with a ferrule for controlling the movement of a guide to focus an objective lens, and the primary body emits a first light beam towards the objective lens along a first axis, the secondary body emits a second light beam along a second axis, a beam controller directs the second light beam through the objective lens along the first axis onto a specific area of the screen, and the optotypes are moved past the path of the first light beam to vary the optotype projected onto the screen, and the matrix is moved past the first light beam.

20 Claims, 4 Drawing Sheets

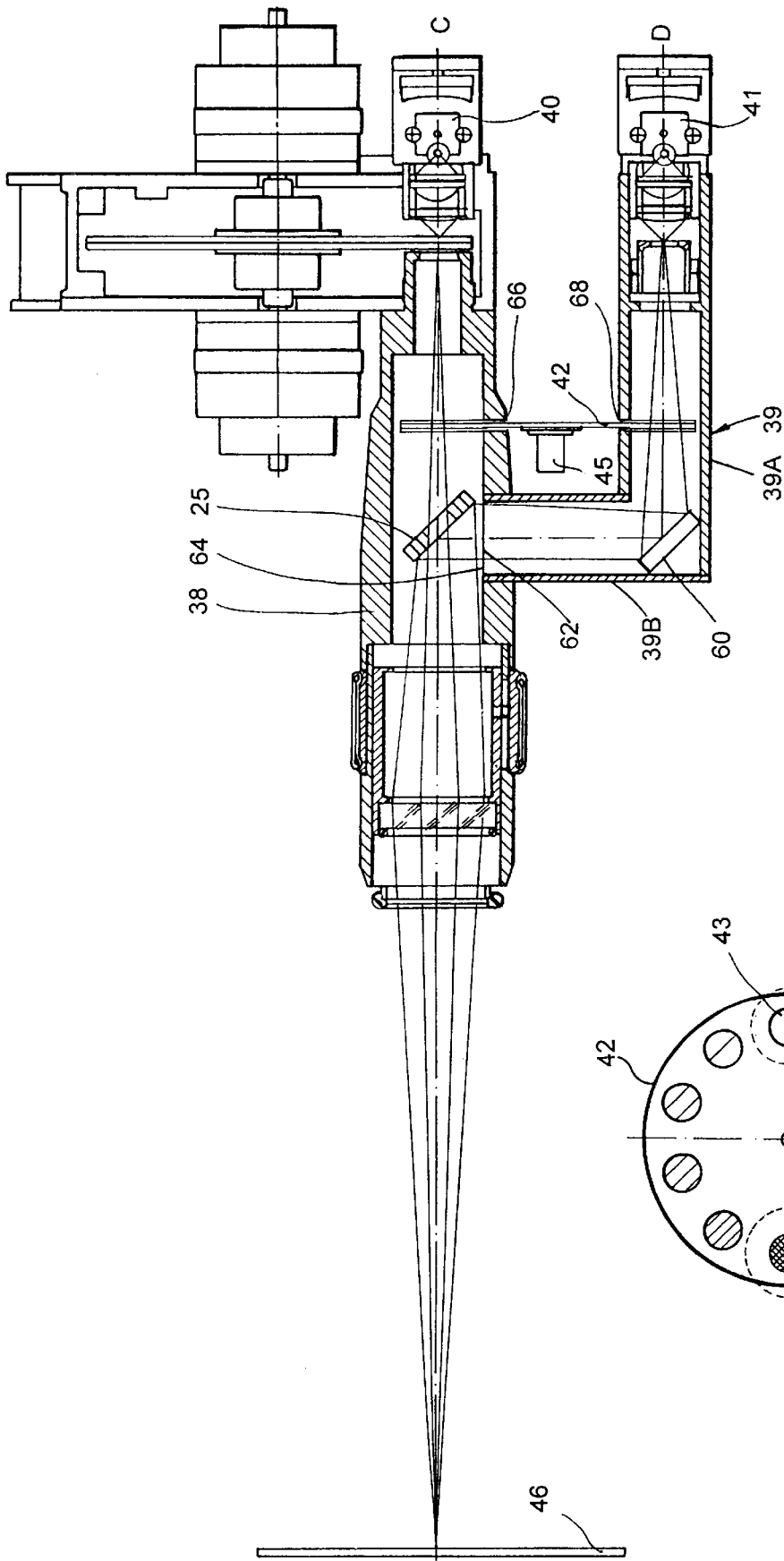

OPTOTYPE PROJECTOR APPARATUS WITH VARIABLE CONTRAST

BACKGROUND OF THE INVENTION

The invention relates to a projector apparatus for projecting optotypes. More particularly, the invention is also concerned with an optotype projector which permits tracking of visual acuity with respect to a varying of a contrast effect.

DESCRIPTION OF THE PRIOR ART

As it is well-known, visual acuity is affected by photometric contrast existing between an object and its background. When the photometric contrast is very high with respect to differences in the retinal illumination which is produced, then even small size objects will be seen. On the contrary, when the photometric contrast is low, or there is a low contrast effect, then even a larger object does not succeed in producing contrasts of such a value so as to make them perceptible by the retina.

At present, a visus or visual examination, particularly when considering the contrast effects, such visual examination can be made only in intermediate gradualities by means of optotypes (sight or visual types) printed on tables or formed of a translucent plate and illuminated at the back or from the rear, by gradually varying distance of the light source. The large overall dimensions of this equipment, which takes up considerable room or space in the laboratory, joined with the need for a wide range of tables, results in slow operative results, because for every graduality and contrasting effect under examination, it is necessary mechanically to displace the lamp.

SUMMARY OF THE INVENTION

The projector apparatus for projecting optotypes according to the invention is intended to overcome the above stated inconveniences as it presents a new equipment which has all of the qualities of optotype projectors now in use. In addition, it offers new and novel performances such as a best definition of the image, a large variety of optotypes which include special tests for the stereoscopic vision of the chromatic balance of coincidence and others. Moreover, under conditions of extreme accuracy and practical results, given the same ground brightness, the projector according to the invention produces contrasting variations of the optotype images according to pre-arranged values operating on the basis of two complementary light sources which are controlled by means of a remote control so that by diminishing the intensity of one source, a consequent increase of the other source takes place.

BRIEF DESCRIPTION OF THE DRAWINGS

FIG. 3 is a modification of two projectors comprising the projector apparatus shown in FIGS. 1 and 2 and shows a view of one projector for projection of optotypes carried out in a modified version illustrating a second embodiment with a rectilinear primary body 38 and a secondary squared up body 36 using a disk 42 for the contemporary transmission of a couple of images of the same optotypes;

FIG. 4 is a sectional view of the sole disk 42 used in the FIG. 3 version; and

DETAILED DESCRIPTION OF THE PREFERRED EMBODIMENTS

Figure 1:
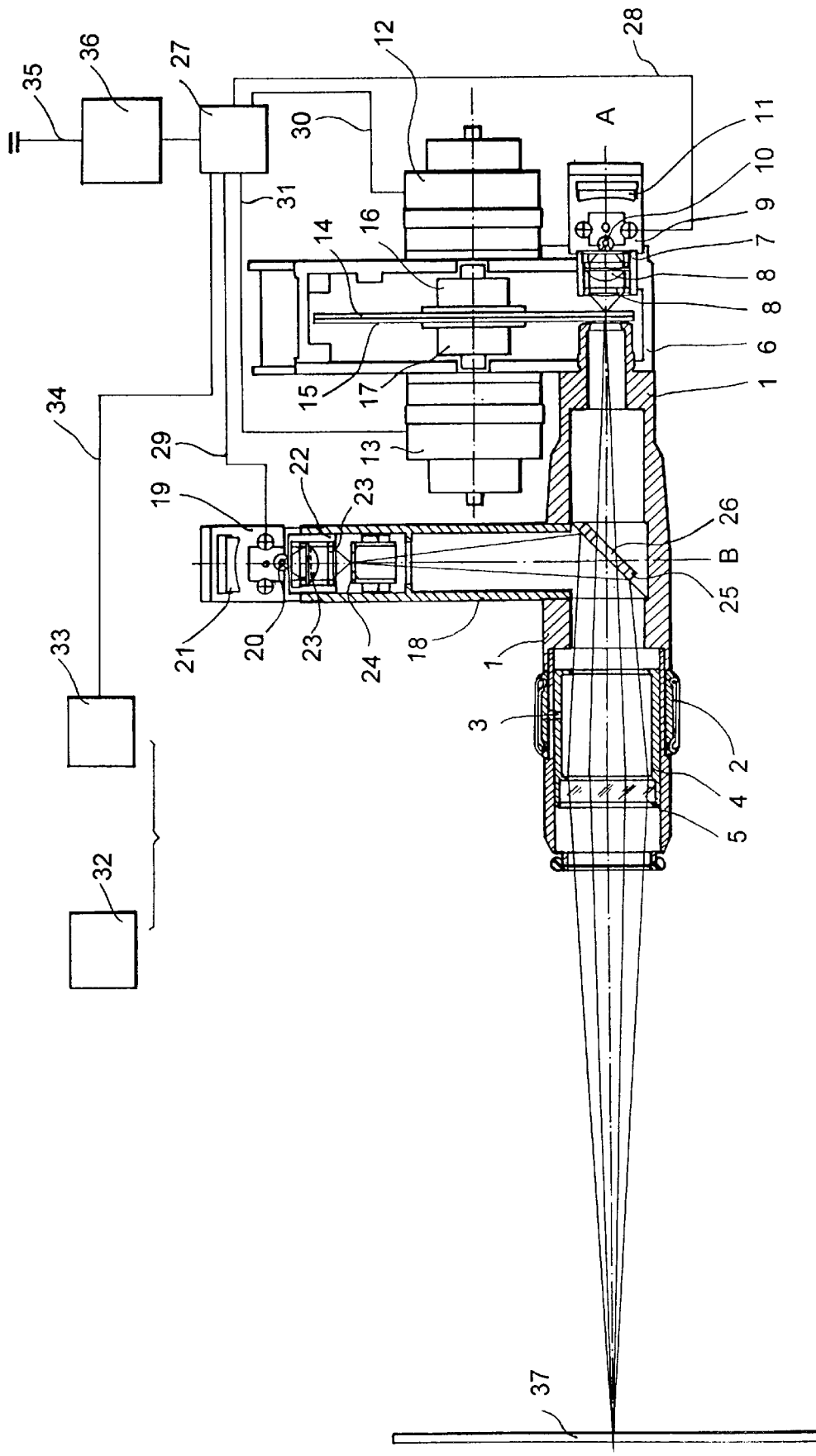
FIG. 1 is a schematic view of one embodiment of the projector apparatus comprising two cooperating projectors, one of which is a basic projector, and the other of which is an image projector, illustrating both an electronic block working system and working operations of the image projector set in a primary body and which provide for a pair of complementary lamps to achieve the formation of an optotype image on a screen.
Figure 2:
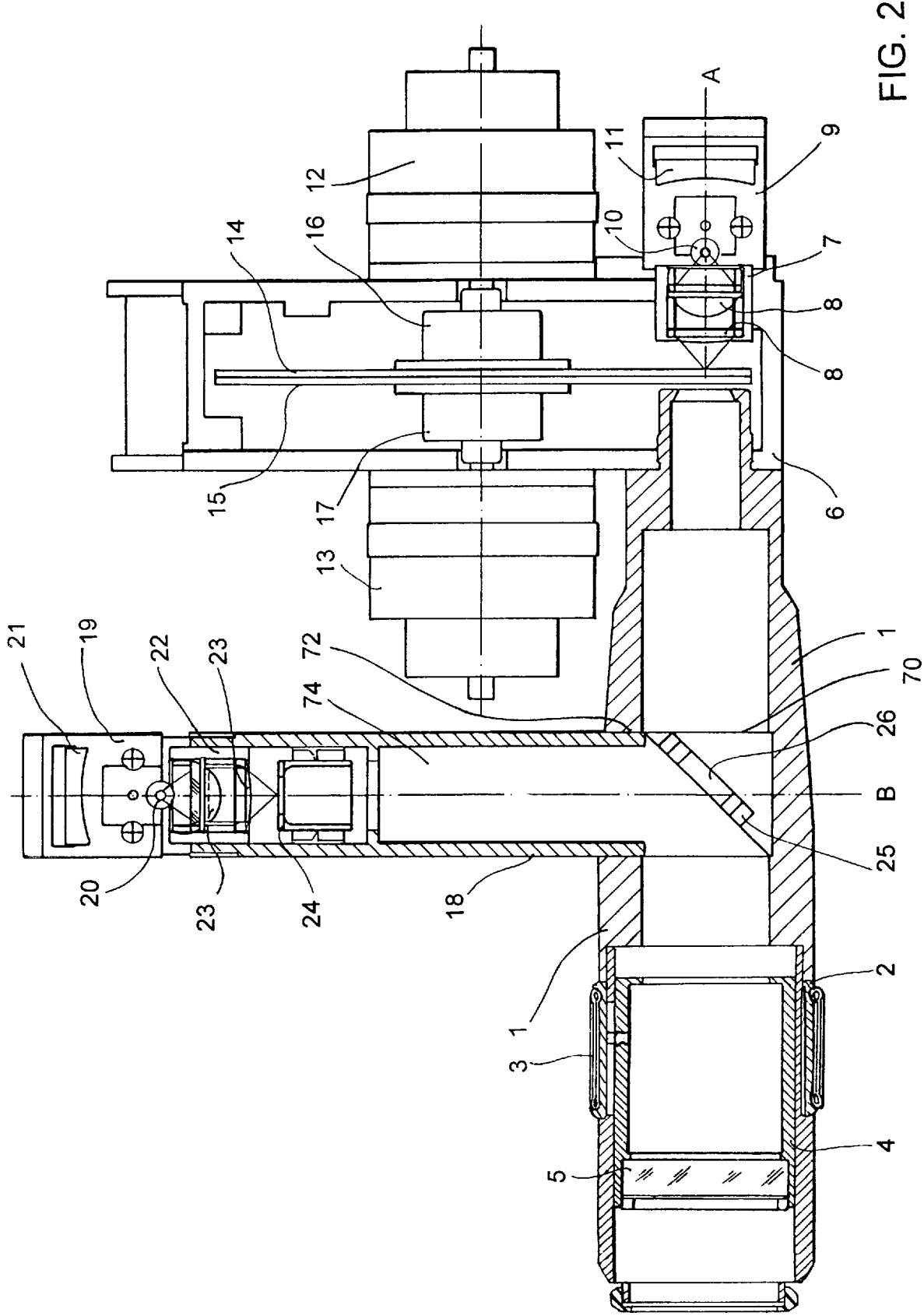
FIG. 2 is an enlarged view of the same projector apparatus of FIG. 1 to illustrate the two projectors without the computer controls.

Referring to the drawings, and in particular to FIGS. 1 and 2 of the accompanying drawings, the optotype projector apparatus comprises a first projector (or basic projector) including a primary body 1, having at a front end thereof, a cylindrical front terminal part provided with a ferrule 2, thereon which ferrule 2 is slidably arranged on a guide 3, for the translation of a support 4 which houses an objective lens 5 and translation of support 4 results in movement of lens 5 for focusing thereof.

A stabilizer 6 has a front end and a rear end, and its front end is provided at and supported on a rear end of primary body 1 and is brought integral on the other terminal end of primary body 1. A support 7 is provided at the other or rear end of stabilizer 6 for supporting a group of optical condensers 8 set axially and axially aligned along a common Axis A. Primary body 1, support 4, lens 5, support 7 and condensers 8 are all axially aligned along central axis A. Stabilizer 6 intermediate its front and rear ends also holds or contains a first light projector including a lampholder 9 for supporting a lamp 10 and a concave mirror 11. The lamp 10 and concave mirror 11 are both also axially aligned with the group of optical condensers 8 along the common axis A.

A frame structure 52 is also supported on stabilizer 6 and has a central axis substantially orthogonally arranged with respect to axis A, and parallel to an axis B of a secondary body 18 of an image projector, and supports first and second motor groups 12, 13 arranged along a common axis substantially parallel to axis A and orthogonal to axis B. Moreover, stabilizer 6 features, on an orthogonal prolongation of the frame structure, motor groups 12 and 13 in a symmetric diagram about the central axis parallel to axis B. Motor group 12 supports a disk 14 coupled with a pinion 16 connected for rotation with motor group 12, and in a similar manner motor group 13 is coupled with a pinion 17 for supporting a disk 15 for rotation therewith. The first motor group 12 provides for rotation of disk 14 which carries matrix forms, and the second motor group 13 provides for rotation of disk 15 with photoengraved optotypes. Disks 14 and 15 have selected panels of optotypes and are counter-situated to allow their position reference during the operative phase. Their laying or positioning relative to each other is determined by pinion 16 located between motor group 12 and disk 14, and by pinion 17 placed or located between motor group 13 and disk 15.

Primary body 1 of the basic projector, in an intermediate thereof position, between objective lens 5 and support 6 is provided with the secondary body 18 of the image projector which is integral with primary body 1 and substantially intermediate the ends thereof, and having one end joined with primary body 1, and its other end provided with another or second light projector which is positioned at the outer end of the secondary body 18. This second light projector, like the previously described first light projector, and also includes a lampholder 19, a lamp 20 and a concave mirror 21. Secondary body 18 is substantially orthogonally oriented relative to primary body 1 and has a longitudinal axis B which is substantially orthogonal to axis A. Support 22 is contained within secondary body 18 and contains a group of optical condensers 23 to focus light emitted from lamp 20 onto a diaphragm 24 which are provided with panels of the same dimensions as the panels of engraved optotypes featured on disk 15.

Within hollow primary body 1 and proximate to secondary body 18 in line with an extension portion indicated at 70 as to where secondary body 18 would extend, there is provided a mirror 25. Secondary body 18 in effect has an opening at the base thereof at the end thereof forming extension 70 joining body 1 and opens into body 1 so that rays projected from lamp 20 impinge onto body 25 provided with a mirrored surface facing lampholder 19 and objective lens 5. Primary body 1 at the outer surface thereof is also provided with an opening 72 in registry with an opening 74 of the secondary body 18. Mirror 25 is provided with a central hole 26 and is positioned at an angle of 45° to the opening of secondary body 18 at the intersection of axes A and B of the primary and secondary bodies, so that mirror 25 bends the rays from lamp 20 through an angle of approximately 90° so that they travel in direction of axis A towards objective 5, while the rays from lamp 10 pass through opening 26.

A microprocessor 27 is provided with four output control lines 28, 29, 30 and 31 and input line coupled to an infra-red receiver 33 by means of line 34. An infra-red remote control is provided to activate infra-red receiver 33 and thereby control microprocessor 27. First line 28 is associated with lamp 10; second line 29 is associated with lamp 20, third line 30 is associated with motor 12 and fourth line 31 is associated with motor 13. These lines cause impulses and controls from microprocessor 27 to operate the elements with which they are associated. Activation and control of microprocessor takes place in response to the infra-red remote control 32 which in turn causes the computer to send information along the output lines 28, 29, 30 and 31.

The system which is activated in response to infrared ray remote control unit 32, transmits to infra-red receiver 33 connected to microprocessor 27 through line 34 to operate microprocessor 27 and thereby the two projectors, as well as the motor 12 and 13. Line 35 is coupled to power supply mains for feeding group 36 which is coupled to microprocessor 27 for powering thereof. Line 28 is coupled to and controls lamp holder 9, and line 29 controls lamp holder 19. Line 30 controls and is coupled to motor 12 for controlling disk 14, and line 31 is coupled to and controls motor 14 for controlling disk 15.

In order to make an examination for visual acuity while also taking into consideration the varying aspects of the contrast effect, by means of remote control 32, the system is activated to determine the quantity of light from lamp 10 forming part of primary projector housed in primary body 1, and the positioning of disks 14 and 15 by control of motors 12 and 13, respectively, on selected engraved optotypes.

Concave mirror 11 and optical condensers 8 aligned along axis A, cooperate with disks 14 and 15 which are rotatable by motors 12 and 13 so that the optotypes pass or traverse across the path along axis A. Both disks 14 and 15 carry the engraved series of optotypes and the relative matrices for determining the formation of images on the background are lighted up by means of lamp 10 and light reflected from concave mirror 11. Then, by rotation of ferrule 2, the focus of objective lens 5 is adjusted to transmit or allow the formation of optotype images onto screen 37 under conditions of maximum contrast. Subsequently, remote control 32 used to activate lamp 20 of secondary projector in secondary body 18, concave mirror 21, the group of optical condensers 23, and the diaphragm 24 direct light energy onto the face of mirror 25 which causes the rays to turn 90° towards objective lens 5, and by means of objective lens 5, the light image delimiting the optotypes is projected onto screen 37. This image is provided or given by the matrix form present on disk 14, which will move consequently to place itself exactly onto the preceding image. As a consequence, by means of remote control 32, it is possible to operate both lamps 10 and 20 at the same time in a complementary way, so that when the intensity of one lamp diminishes the other one increases. Thus obtaining on the screen 37 is provided with an optotype image, in presence of the same background brightness, while variation of the control value of the optotype image is obtained. In this way, the emanation of the visual acuity on different contrast levels is obtained on screen 37.

Referring now to FIGS. 3 and 4, and more particularly to FIG. 3 which is a modification of the projector in FIG. 1, and in which like parts, the same as those in FIG. 1 were left unnumbered, and the additional and different parts are numbered, the optotype projector includes a rectilinear primary body 38 which is a modification of the primary body 1 shown in FIG. 1, aligned on an axis C together with a main or primary projector 40. In addition, there is provided a secondary squared up body 39 housing a secondary projector 41 aligned on an axis D which is parallel to axis C.

Primary body 38 is substantially similar to primary body 1 and contains all of the elements in FIG. 1 including mirror 25 provided with central hole 26. Secondary body 39 is also generally similar to secondary body 19 and contains all of the elements as in FIGS. 1 and 2. Secondary body is an L-shaped member and includes a first section 39A and a second section 39B which are orthogonally connected with each other. First section 39A is coaxial with axis D, and second section 39B is orthogonal to axes C and D. Positioned within the interior of secondary section 39 at the corner where first and second sections 39A, 39B join each other is a mirror 60 at an angle of 45° to axis D to turn the ray;s projected the lamp in secondary projector 41 through an angle of 90°.

Secondary section 39B is provided with an exit port or outlet opening 62 which is aligned with an opening 64 in primary body 38 so that rays from the secondary projector are rotated by mirror 60 through an angle of 90° and travel through first section 39A and impinge onto mirror 25 as they exit from outlet opening 62 and are rotated by mirror 25 through an angle of 90° and exit from primary body 38 through objective lens 5. Mirror 60 is located at an elbow of said L-shaped secondary body at the joinder of said first and second sections.

Both the primary body 38 and the secondary body 39 along second portion 39B are provided with a cut out portion 66 and 68 to receive a disk 42 which is coupled to group motor 45 to rotate disk 42 so that it rotates past axes C and D so that it rotates past the rays produced in primary projector 40 and secondary projector 41.

As best seen in FIG. 4, disk 42 is shown, carrying a counterpoised double series of grey filters each having a different absorption gradation between a through hole 43 and a shutter 44 aligned along a diameter of disk 42. Disk 42 is orthogonally related to both axis C of primary body 38 and axis D of first section 39A secondary body 39 so that axis C will pass through the center of through hole 43 when the axis D passes through the center of shutter 44. Group motor 45 is operated by microprocessor 27 under the control of remote control 32 as in the FIG. 1 embodiment to cause the rotation of disk 42 thus obtaining in a sequence, on a screen 46, the image of the optotype with a contrast scalarity maintaining a constant brightness of the background.

Figure 5:
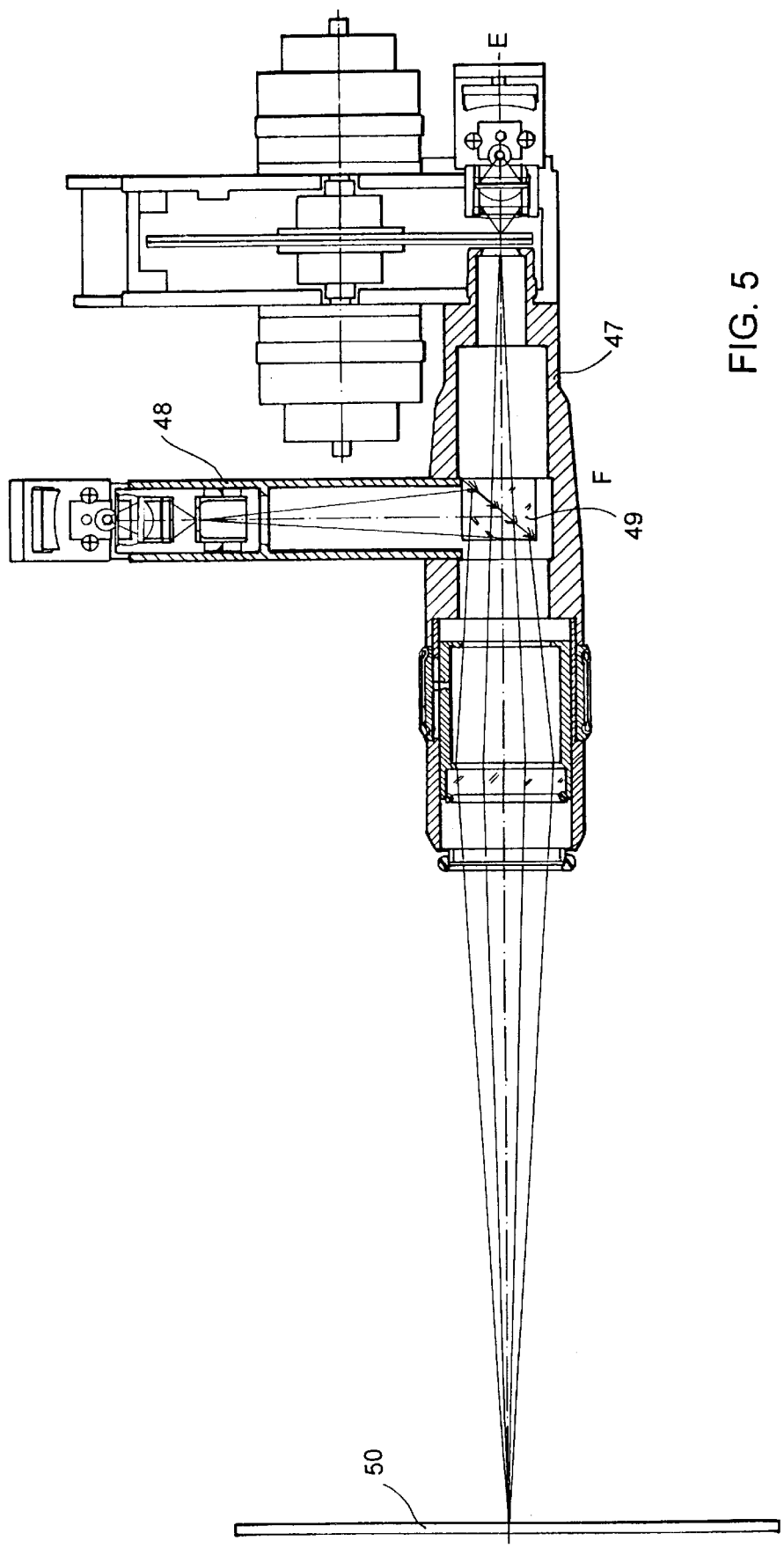
FIG. 5 is a view of a third embodiment of the optotype projector apparatus which utilizes a primary body 47 and a secondary body 48 orthogonally related to each other together with a glass beam separator body 49 at the intersection of their axes E and F.

Referring now to FIG. 5 which illustrates another embodiment according to the invention, and includes primary body 47 and secondary body 48 having a longitudinal axis F orthogonal to axis E of primary body 47. Longitudinal axis E, and longitudinal axis F are orthogonal to each other. In this embodiment, the same elements which are described in FIGS. 1 and 2 remain un-numbered, but perform the same function as like or corresponding parts in FIGS. 1 and 2.

In this embodiment, the optotype projector in primary body 47 and secondary body 48 are generally similar to the embodiment shown in FIGS. 1 and 2, include a glass beam separator 49 in lieu of mirror 25 with central hole 26 positioned at an angle of 45°, at the intersection of axes E and F of bodies 47 and 48, and making the contemporary light transmission and the image reflection at 50% onto screen 50. The microprocessor and the infra-red controls shown in FIG. 1 have been omitted, but the same controls are used in this embodiment. Glass beam separator permits the light transmission from the first lamp to pass therethrough and the light from the first lamp to be rotated through an angle of 90° for exiting through objective lens 5.

While there has been shown what are considered to be the preferred embodiments of the invention, it would be obvious to those skilled in the art that various changes and modifications may be made without departing from the scope of the invention.

What is claimed is:

1. An optotype projector apparatus provided with variable contrast comprising:

a primary body (1, 38, 47) including a frame structure at a rear end thereof, said primary body at a front end thereof being provided with an opening, a ferrule (2) and a guide (3), said ferrule being set on a cylindrical front terminal part of said primary body at the front end thereof, in a sliding relationship on said guide (3);

a first support (4) and an objective lens (5) carried by said first support and said objective lens (5) being translated by the movement of said first support (4) for focusing of said objective lens, and a stabilizer (6) brought integral on a rear terminal part of said primary body;

a second support (7) and a group of first optical condensers (8) supported by said second support (7) set axially, said second support holding a first light projector comprising a first lamp (10) and a first concave mirror (11) for projecting a first light beam;

a secondary body (18, 39, 48) coupled with said primary body at an intermediate position thereof, said primary body in said intermediate position thereof being integral and orthogonally arranged with said secondary body (18);

said secondary body having at an outer end thereof a second light projector comprising a second lamp (20) and a second concave mirror (21);

a beam controller positioned at an angle of 45° at an intersection of axes of said primary and said secondary bodies;

said first light projector projecting light towards said beam controller for transmission to said objective lens and passing through said opening;

a support (22) to support a group of second optical condensers (23) for focusing the light from said lamp (20) solely onto a diagram (24), and projecting light from said lamp (20) onto said beam controller;

optotype means cooperating with said first light projector and a first light beam for passing panels of photo-engraved optotypes past said first light beam;

a remote control (32) operatively associated with and remotely controlling a microprocessor for making an examination of visual acuity, while considering a varying of a contrast effect, for activating and thus determining the quality and intensity of lighting of said first lamp (10) projected by said first projector transmitting the light through a selected optotype;

said first concave mirror (11), said first optical condensers (8), said optotype means, and said first lamp together determining the formation of images on a background member of said beam controller to be lighted up, and rotation of said ferrule (2) and focusing of said objective lens (5) thus forming optotype images onto a screen (37) under conditions of maximum contrast;

said microprocessor (27) being coupled with said second lamp (20) for activation thereof in response to said remote control (32), and said second group of optical condensers (23), and the (24) causes the light from said lamp (20) to be projected onto said beam controller and directed to said objective lens (5), and a light image delimiting the optotypes projected onto said screen (37); and said remote control (32) activates both said lamps (10) and (20) to operate said lamps (10) and (20) at the same time in a complementary way, so that when the intensity of one lamp diminishes then the intensity of the other lamp increases as a consequence thus obtaining on the screen (37) a uniform brightness on said background member, a variation of a control value of the optotype image and permitting an examination of the visual acuity on different contrast levels.

2. The optotype projector apparatus as claimed in claim 1, wherein said beam controller includes said background member having a mirrored surface and a central hole, light projected from said first light projector lamp passing through said central hole, and light from said second light projector impinges onto said mirrored surface and is directed towards said objective lens and to said screen; and including first and second motors (12, 13) positioned on an orthogonal prolongation of said frame structure, in a symmetric diagram, a first disk (14) carrying matrix forms coupled with said first motor (12) for rotation of said first disk (14), and a second disk (15) carrying panels of photo-engraved optotypes (15) coupled with said second motor (13) for rotating said second disk (15) the photo-engraved optotypes;

said disks (14, 15) being countersituated to allow a position reference for said disks during an operative phase and where their laying is determined by a first pinion (16) located between the first motor (12) and the disk (14) and by another pinion (17) placed between the second motor (13) and the disk (15);

said diaphragm 24 having panels of the same dimensions as the photo-engraved optotypes panels, provided on said second disk (15);

said remote control (32) controlling said motors (12,13) for controlling the positioning of said disks (14, 15) to transmit the light through the selected optotype;

said disk (15) carrying the engraved series of optotypes and said disk (14) carrying the relative matrices and said first lamp together determining a formation of images on the background element to be lighted up; and said microprocessor (27) controlling said disks (14,15) controlling the optotypes projected onto said screen (37), the image being formed by the matrix form present on disk (14) which will move consequently to place itself exactly on the preceding image.

3. The projector apparatus according to claim 1, including means including lines (28,29,30,31) coupling said microprocessor to said first and second lamps and said first and second motors; and means including a receiver (33) coupled with said microprocessor (27) responsive to said remote control (32) for activating said projectors, said remote control transmitting an infrared ray to said receiver (33), and means including a line (34) coupled with said microprocessor (27) and a feeding group (36) coupled with a mains supply by a line (35) to said microprocessor.

4. The projector according to claim 1, wherein said primary body includes a rectilinear primary body (38);

said secondary body is a squared up body housing (39);

said primary body being aligned along a first axis and includes a main projector (40);

said secondary projector being aligned along a second axis and includes secondary projector (41), said first and second axes being substantially parallel to each other;

said optotype means including a disk (42) carrying a counterpoised double series of grey filters each having a different absorption gradation when passing between a through hole (43) and a shutter (44); and a motor group (45) operated by said microprocessor responsive to activation by said remote control for causing rotation of said disk (42) for obtaining in a sequence, on a screen (46), an image of the optotype with a contrast scalarity maintaining a constant brightness of the background element.

5. The projector apparatus according to claim 1, wherein the axes of said primary body and the axis of said secondary body intersect at an intersection point, said beam controller includes a glass beam separator (49) associated with said primary body (47) and said secondary body (48), said glass beam separator being positioned at an angle of 45° at the intersection point of the axes of said primary body (47) and said secondary body (48) and making contemporary light transmission and image reflection at 50% of said screen (50).

6. An optotype projector apparatus provided with variable contrast, comprising:

a primary body and a secondary body each having a hollow interior and each enclosing light projecting means, said primary body having a first central axis and said secondary body having a second central axis;

said primary body including at one end thereof a support for an objective lens, a guide for said support and being provided with means for movement of said support in said guide, and a ferrule for controlling the movement of said guide for focusing of said objective lens;

said primary body including at the other end first light projecting means for emitting a first light beam towards said objective lens along said first axis for impingement onto a specific area of a screen;

said secondary body including one end provided with second light projecting means for emitting a second light beam along said second axis;

beam controller means coupled with said primary body and said secondary body for directing said second light beam through said objective lens along said first axis onto said specific area of said screen; and optotype means and matrix means, means for movement of said optotype means including an optotype holder containing optotypes past the path of said first light beam to vary the optotype projected onto said screen and means for movement of said matrix means including a matrix past the path of said first light beam.

7. The projector apparatus as claimed in claim 6, wherein the axes of said primary and said secondary body are orthogonally related and said beam controller includes a member having a full mirrored surface.

8. The projector apparatus as claimed in claim 6, wherein the axes of said primary and said secondary bodies each having a central axis parallel to each other.

9. The projector apparatus as claimed in claim 6, wherein said optotype means includes a first support associated with said primary body and said matrix means includes a second support coupled with said primary body, a first disk supported by said first support and rotatable past said light projecting means of said primary body and a second disk supported by said second support and rotatable past said light projecting means of said primary body, said first disk carrying optotype forms and said second disk carrying matrix forms, said light projecting means of said primary body and said secondary body with said disks controlling the images to be projected onto said screen, and control means for controlling the light projected from each of said light projecting means and the rotation of said disks.

10. The projector apparatus as claimed in claim 6, wherein said optotype means includes a disk carrying a counterpoised double series of grey filters, and including means for rotating said disk past each of said first and said second light projecting means.

11. The projector apparatus as claimed in claim 6, wherein said first axis and said second axis intersect with each other at an intersection point, and said beam controller means includes a mirror located at said intersection point at an angle of 45° to said first and said second axis of said primary and said secondary body.

12. The projector apparatus, as claimed in claim 6, wherein said secondary body is an L-shaped member and includes a first section and a second section each having a first center axis and a second center axis, respectively, orthogonally related to each other, the first center axis of said first section being parallel to the first central axis of said primary body, and the second center axis of said second section being orthogonal to said first central axis and said first center axes of said first section; said second section being joined both to said primary body and said first section and an inlet opening at another end and having an outlet opening at one end thereof, said outlet opening into said primary body and aligned with an opening in said primary body and joined to said primary body at said primary body opening, and said inlet opening into said first section.

13. The projector apparatus, as claimed in claim 12, wherein said beam controller includes a first mirror and a second mirror, said first mirror being proximate to said inlet opening of said primary body and inclined at an angle of 45° to said first central axis and being proximate to said second center axis of said second section, said second mirror being aligned at an angle of 45° to said first and said second axes of said first and second sections and being positioned at an elbow of said L-shaped member for rotating the light from said second light projecting means through an angle of 90°.

14. The projector apparatus as claimed in claim 6, wherein said primary body and said secondary body each have a hollow interior and are orthogonally connected to provide for a pathway between said first and said second primary holes, said beam controller means being disposed along an angle of 45° the a hollow interior of each of said primary body and said secondary body in the pathway between said first and said second primary bodies; said beam controller including a mirror surface for directing said second light beam from a first direction substantially parallel to said objective lens to a second direction orthogonal to said objective lens, and said beam controller having hole through which said first light beam passes.

15. The projector apparatus as claimed in claim 6, wherein said primary body is axially aligned along a first axis, said secondary body includes first and second sections orthogonally related and joined at a common joint to each other, said first section and said primary body each having a central axis in parallel with and spaced from each other, said second section having a central axis orthogonal to the central axes of said primary body and said first section, said primary body being provided with an opening in a wall thereof and said second section having an exit port joined with said opening, said beam controller means includes a first light direction changing source in said secondary body at the common joint of said first and second sections for changing the direction of the light to direct the light to said exit port, and a second light direction changed source for changing the direction of light exiting from said port and directing the light towards said objective lens.

16. The projector apparatus as claimed in claim 6, wherein said beam controller means includes a glass beam separator for directing beams from said first light projecting means therethrough to said lens and for changing direction of beams from said second light projecting means onto said lens.

17. The projector apparatus according to claim 16, including a microprocessor and means coupling said microprocessor to said first and second light projecting means, first and second motors including four controller lines, a first of said four controller lines controlling a receiver coupled with said microprocessor responsive to a remote control for activating said first light projecting means by means of an infrared ray which transmits said infrared ray to said receiver and a second of said four controller lines being coupled with said microprocessor and said second light projecting means for activation thereof and a feeding group coupled with a means supply and coupled to said microprocessor, the other control lines controlling the movement of said optotype means and the matrix.

18. The projector apparatus according to claim 6, wherein a secondary body, and said beam controller means includes a glass beam separator coupled with said primary body and said secondary body positioned at an angle of 45° at the intersection point of the intersecting axes of said primary body and said secondary body making the contemporary light transmission and the image reflection at 50% of screen 50.

19. An optotype projector apparatus provided with variable contrast for producing contrasting variations of optotype images according to pre-arranged values operating on the basis of two complementary light sources remotely controlled whereby a diminishing of intensity one of the light sources produces a consequent increase of the other of the light sources, comprising:

a primary body including a frame structure at a rear end thereof, said primary body at a front end thereof being provided with an opening, a ferrule and a guide, said ferrule being set on a cylindrical front terminal part of said primary body at the front end thereof, in a sliding relationship on said guide;

a secondary body angularly coupled with said primary body at an intermediate position thereof, said primary body in said intermediate position thereof being integral and orthogonally arranged with said secondary body;

a first support and an objective lens carried by said first support and said objective lens being translated by the movement of said first support for focusing of said objective lens, and a stabilizer brought integral on a rear terminal part of said primary body;

a second support and a group of first optical condensers supported by said second support set axially, said second support holding a first light projector comprising a first lamp and a first concave mirror for projecting a first light beam;

said secondary body having at an outer end thereof a second light projector comprising a second lamp and a second concave mirror;

a beam controller positioned at an angle of 45° at an intersection of axes of said primary and said secondary bodies;

said first light projector including means for projecting light towards said beam controller for transmission to said objective lens and passing through said opening;

a support to support a group of second optical condensers for focusing the light from said lamp solely onto a diagram, and projecting light from said lamp onto said beam controller;

optotype means cooperating with said first light projector and a first light beam for passing panels of photo-engraved optotypes past said first light beam;

a remote control operatively associated with and remotely controlling a microprocessor for examining visual acuity on different contrast levels, while considering a varying of a contrast effect, for activating and thus determining the quality and intensity of lighting of said first lamp projected by said first projector by transmitting the light through a selected optotype;

means including said first concave mirror, said first optical condensers, said optotype means, and said first lamp together for determining the formation of images on a background member of said beam controller to be lighted up, and means for rotation of said ferrule and for focusing of said objective lens thus forming optotype images onto a single screen under conditions of maximum contrast;

said microprocessor being coupled with said second lamp for activation thereof in response to said remote control, and said second group of optical condensers, and the diagram causes the light from said lamp to be projected onto said beam controller and directed to said objective lens, a light image delimiting the optotypes projected onto said screen; and said remote control controlling activates both said first and said second lamps to operate said lamps and at the same time in a complementary way to provide for complementary light sources, so that when the intensity of one lamp diminishes then the intensity of the other lamp increases as a consequence thus obtaining on the screen a uniform brightness on said background member, a variation of a control value of the optotype image and permitting an examination of the visual acuity on different contrast levels.

20. The optotype projector apparatus according to claim 19, wherein:

said primary body and said secondary body each have a hollow interior and for enclosing light projecting means in the form of said first and second lamps, said primary body having a first central axis and said secondary body having a second central axis;

said primary body including send first light for projecting a first light beam towards said objective lens along said first axis for impingement onto a specific area of said single screen;

said secondary body including one end provided with said second light for emitting a second light beam along said second axis;

said beam controller being coupled with said primary body and said secondary body for directing said second light beam through said objective lens along said first axis onto said specific area of said single screen; and said remote control including, means for movement of an optotype holder containing optotypes past the path of said first light beam to vary the optotype projected onto said single screen and means for movement of a matrix past the path of said first light beam, whereby the bright contrast is projected onto said single screen to form a projection display with a variable bright contrast on projected visual texts.

* * * * *